United States Patent
Feng et al.

(10) Patent No.: US 9,834,530 B2
(45) Date of Patent: Dec. 5, 2017

(54) 3-FURYL-2-CYANO-2-ACRYLAMIDE DERIVATIVE, PREPARATION METHOD THEREFOR, PHARMACEUTICAL COMPOSITION AND USE THEREOF

(71) Applicant: JENKEM TECHNOLOGY CO., LTD. (BEIJING), Haidan District, Beijing (CN)

(72) Inventors: Zewang Feng, Beijing (CN); Jianhuan Jia, Beijing (CN); Yan Liu, Beijing (CN); Zhenguo Wang, Beijing (CN); Xuan Zhao, Beijing (CN)

(73) Assignee: Jenkem Technology Co., Ltd. (Beijing), Beijing (CN)

( * ) Notice: Subject to any disclaimer, the term of this patent is extended or adjusted under 35 U.S.C. 154(b) by 0 days.

(21) Appl. No.: 15/170,871

(22) Filed: Jun. 1, 2016

(65) Prior Publication Data
US 2016/0272604 A1    Sep. 22, 2016

Related U.S. Application Data

(63) Continuation of application No. PCT/CN2014/092647, filed on Dec. 1, 2014.

(30) Foreign Application Priority Data

Dec. 2, 2013 (CN) .......................... 2013 1 0632184

(51) Int. Cl.
*C07D 307/54* (2006.01)
*C07D 405/12* (2006.01)
*C07D 307/46* (2006.01)

(52) U.S. Cl.
CPC ......... *C07D 307/54* (2013.01); *C07D 307/46* (2013.01); *C07D 405/12* (2013.01)

(58) Field of Classification Search
USPC ................................. 514/414, 432, 740, 741
See application file for complete search history.

(56) References Cited

FOREIGN PATENT DOCUMENTS

WO    WO 2012103282 A2 *   8/2012   ........... A61K 39/395

OTHER PUBLICATIONS

Tarleton (Biorganic & Medicinal Chemistry, 21 (2013) 333-347; Published online Oct. 23, 2012).*

* cited by examiner

*Primary Examiner* — Pancham Bakshi
(74) *Attorney, Agent, or Firm* — Zareefa B. Flener; Flener IP Law

(57) ABSTRACT

Disclosed are a 3-furyl-2-cyano-2-acrylamide derivative with epidermal growth factor receptor (EGFR) inhibitory activity and pharmaceutical acceptable salt thereof, together with preparation method thereof, pharmaceutical composition comprising the compound, and application of the compound in treating senile dementia (AD). The new compound is shown as formula I, wherein $R_1$ is selected from the group consisting of H, $C_1$-$C_6$ alkyl, $C_2$-$C_6$ alkenyl, $C_2$-$C_6$ alkynyl and $C_3$-$C_6$ cycloalkyl; $R_2$ is selected from the group consisting of alkyl, cycloalkyl, alkenyl, alkynyl, aryl, heteroaryl, aralkyl and heteroaralkyl; X is selected from the group consisting of $CH_2$, NH, O and S; m and n are all integers greater than or equal to zero.

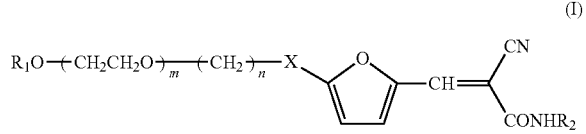

14 Claims, 1 Drawing Sheet

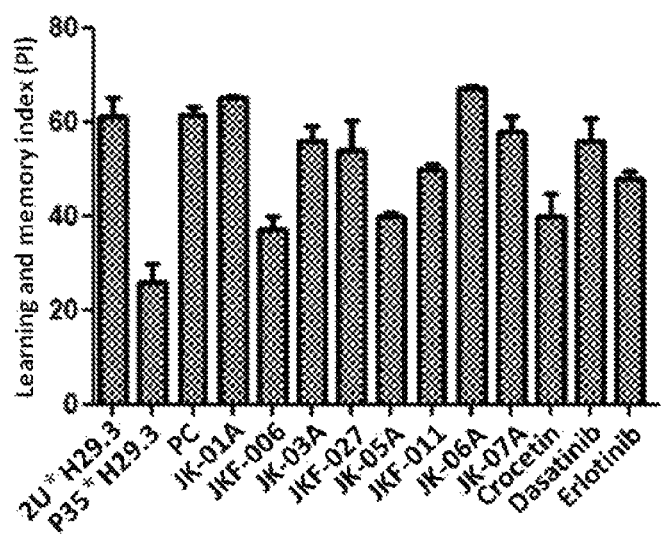

3-FURYL-2-CYANO-2-ACRYLAMIDE DERIVATIVE, PREPARATION METHOD THEREFOR, PHARMACEUTICAL COMPOSITION AND USE THEREOF

CROSS-REFERENCE TO RELATED APPLICATION

The application is a continuation of PCT/CN2014/092647 (filed on Dec. 1, 2014), which claims priority from CN Patent Application Serial No. 201310632184.9 (filed on Dec. 2, 2013), the entire contents of which are incorporated herein by reference for all purposes.

FIELD OF THE INVENTION

The present invention is related to a 3-furyl-2-cyano-2-acrylamide derivative with epidermal growth factor receptor (EGFR) inhibitory activity, preparation method thereof, application thereof, pharmaceutical composition comprising the compound, additionally, the present invention is further related to use of 3-furyl-2-cyano-2-acrylamide derivative in treatment of senile dementia (AD).

BACKGROUND OF THE INVENTION

Senile dementia (also known as Alzheimer's disease, AD) is a common central nervous system degenerative disease, patients suffer from recent memory disorders, followed by persistent intelligence recession, loss of judgment and reasoning ability, dyskinesia, etc. As early as in 1976, Davies et discovered the phenomenon of dysfunction and apoptosis in central neurons and synapses particularly those involved in cholinergic neurons in AD patients. With the development of molecular biology, genes associated with AD which have been discovered include APP (amyloid precursor protein), PS1 (presenilin-1), PS2 (presenilin-2), ApoE4 and Cytochrome oxidase I and II encoded by mitochondrial, etc. The main pathological changes of AD are a regional neuronal loss and brain tissue atrophy, a large number of amyloid plaques appeared, also known as senile plaques (SP) and deposition of neurofibritary tangles, surrounded by dystrophic neuritis, activated microglia and astrocytes. The degree of dementia of an AD patient is positively correlated with developing of amyloid plaques. The main component of senile plaques is β-amyloid peptide: Aβ42, having a molecular weight of about 4.2 KD and consisting of 39~43 amino acid residues, being formed from amyloid precursor protein (APP), a complete APP is Type I transmembrane protein which may be hydrolyzed by α-secretase or β-secretase, then disintegrated in the extracellular domain to produce sAPPα(soluble APP)/sAPPβ and CTFα(C-terminal fragments)/CTFβ, and CTFα/CTFβ could be cut by γ-secretase to produce a series of Aβ and CTFγ with different molecular sizes, mostmutations of PS could result in an increased production of Aβ42 through their effect on γ-secretase (may be a component of γ-secretase).

As shown in the investigation for health-threatening epidemics, the degree of concern for AD has leapt to the front position in senile diseases, and AD becomes a disease with a high incidence threatening the life and health of the elderly only next to cardiovascular disease, cancer, brain death. Although scientists have studied AD for many years, this disease, the most commondementia, is still uncurable. Currently the drugs for AD on the market can only improve the symptoms of AD patients, slow but not prevent or reverse the progression of disease. Therefore, the development of new drugs aimed at the etiology of AD disease not new mechanisms of symptoms is still the key research directions of domestic and foreign pharmaceutical companies.

Aβ42 plays a key role in occurrence and development of AD, and the current further researches of metabolism and toxicity of Aβ42 provide a wide range of potential drug targets for the treatment of AD. In WO2012/103282, ZHONG Yi reported a preferred target for the treatment of Alzheimer's disease—the epidermal growth factor receptor (EGFR) screened by employing transgenic fruit flies and double transgenic mice. Inhibition of EGFR could improve the condition of early memory loss of transgenic fruit flies and miceinduced by Aβ42, the pharmacological activity screening data showed an effectiveness of EGFR inhibitors which have been used clinically (such as gefitinib, erlotinib, lapatinib, canertinib) and EGFR inhibitors being studied (such as EKB-569, CL-387785, HKI-272, BIBW 2992, HKI-357, ZD-6474, AEE 788, XL647, BMS-599626, IPI-504, 17-AAG, JKF-006, JKF-011, JKF-027, GJ-06, GJ-06-1, GJ-12, GJ-12-1) in the treatment of Aβ42-induced memory loss of transgenic fruit flies and double transgenic mice with expression of Aβ42. The patent screened three compounds JKF-006, JKF-011, JKF-027 with a preferable curative effect.

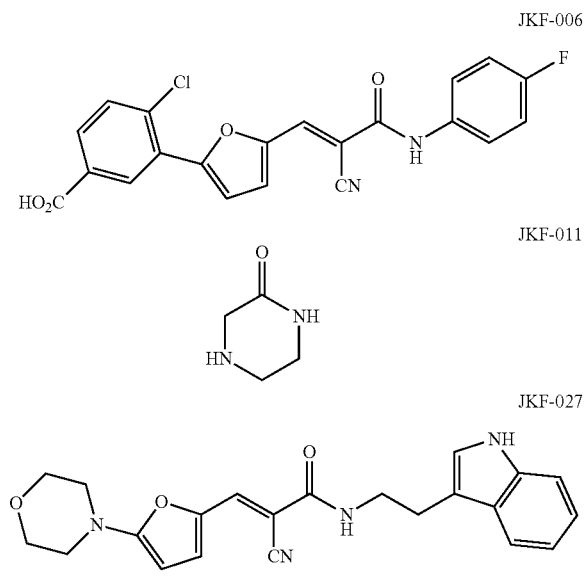

In the present invention, the structure of compounds JKF-006, JKF-027 disclosed in WO2012/103282 is modified to produce to a series of 3-furan-2-cyano-2-acrylamide derivatives, and some of these derivatives have anti-Alzheimer's disease activities significantly higher than those of compounds JKF-006, JKF-027 disclosed in WO2012/103282 and the difference is significant, discovered in the activity-screening study for transgenic fruit flies.

SUMMARY OF THE INVENTION

One aspect of the present invention is to provide a 3-furyl-2-cyano-2-acrylamide derivative shown as formula (I), or a pharmaceutical acceptable salt thereof:

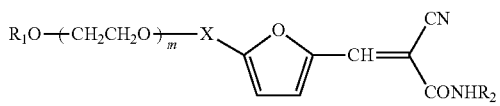

I wherein $R_1$ is selected from the group consisting of H, $C_1$-$C_6$ alkyl, $C_2$-$C_6$ alkenyl, $C_2$-$C_6$ alkynyl and $C_3$-$C_6$ cycloalkyl; $R_2$ is selected from the group consisting of alkyl, cycloalkyl, alkenyl, alkynyl, aryl, heteroaryl, alkaryl, aralkyl and heteroaralkyl, which are substitutedor unsubstituted by halogen; X is $(CH_2)_n$ or $(CH_2)_nY$, wherein n is an integer greater than or equal to zero; Y is NH, O or S; m is an integer greater than or equal to zero.

In an embodiment of the present invention, in the general formula (I) X is $(CH_2)_n$, wherein n is an integer greater than zero, preferably n is an integer of 1-10, more preferably n is an integer of 1-5, and more preferably n is 1, 2, 3, 4 or 5.

In an embodiment of the present invention, in the general formula (I) X is $(CH_2)_nY$, wherein n is an integer greater than or equal to zero, preferably n is an integer of 0-10, more preferably n is an integer of 0-5, and more preferably n is 0, 1, 2, 3, 4 or 5; Y is NH, O or S, preferably Y is NH.

In an embodiment of the present invention, in the general formula (I) X is $(CH_2)_nY$, wherein n is 0, 1, 2, Y is NH, preferably X is NH, $CH_2NH$.

In an embodiment of the present invention, in the general formula (I) m is an integer of 0-10, preferably m is an integer of 0-5, and more preferably m is 0, 1, 2, 3, 4 or 5.

In an embodiment of the present invention, in the general formula (I) $R_1$ is selected from H, $C_1$-$C_6$ alkyl, preferably H, $C_1$-$C_3$ alkyl, more preferably H, methyl, ethyl.

In an embodiment of the present invention, in the general formula (I) $R_2$ is selected from the group consisting of $C_1$-$C_{10}$ alkyl, $C_3$-$C_{10}$ cycloalkyl, $C_2$-$C_{10}$ alkenyl, $C_2$-$C_{10}$ alkynyl, $C_6$-$C_{15}$ aryl, $C_6$-$C_{15}$ heteroaryl, $C_6$-$C_{15}$ alkylaryl, $C_6$-$C_{15}$ aralkyl and $C_6$-$C_{15}$ heteroaralkyl, preferably, $R_2$ is selected from the group consisting of $C_6$-$C_{15}$ aryl, $C_6$-$C_{15}$ heteroaryl, $C_6$-$C_{15}$ alkylaryl, $C_6$-$C_{15}$ aralkyl and $C_6$-$C_{15}$ heteroaralkyl.

More preferably, in an embodiment of the present invention, in the general formula (I) $R_2$ is selected from halophenyl, more preferably, $R_2$ is selected from fluorophenyl, chlorophenyl, bromophenyl, most preferably, $R_2$ is selected from p-fluorophenyl, p-chlorophenyl, p-bromophenyl.

More preferably, in an embodiment of the present invention, in the general formula (I) $R_2$ is selected from

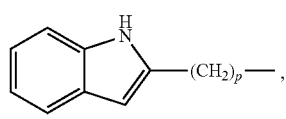

wherein p is an integer of 0-5, more preferably, p is an integer of 0-3, most preferably, p is 0, 1, 2, 3.

In an embodiment of the present invention, the compound of the general formula (I) is:

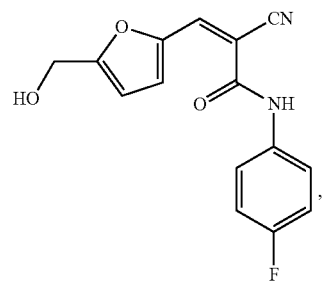

JK-01A

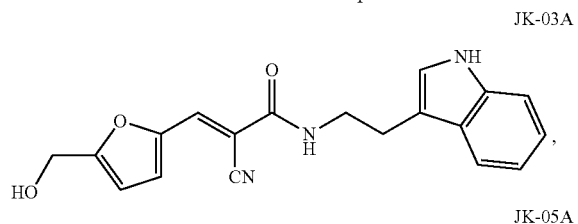

JK-03A

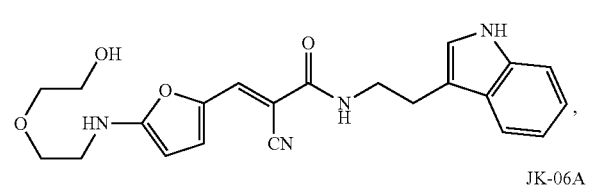

JK-05A

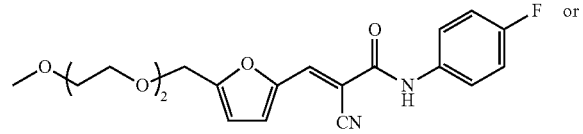

JK-06A

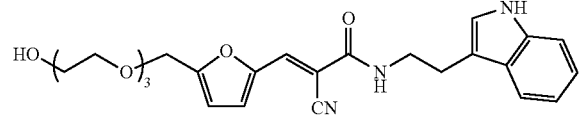

JK-07A

The present invention also relates to use of a 3-furan-2-cyano-2-acrylamide derivative shown as formula (I) or a pharmaceutically acceptable salt thereof in the manufacture of a medicament for the treatment or prophylaxis of senile dementia (AD). Furthermore, the present invention also relates to use of a 3-furan-2-cyano-2-acrylamide derivative shown as formula (I) or a pharmaceutically acceptable salt thereof in the manufacture of a medicament for the treatment or prophylaxis of neurodegenerative diseases. Furthermore, the present invention also relates to use of a 3-furan-2-cyano-2-acrylamide derivative shown as formula (I) or a pharmaceutically acceptable salt thereof in the manufacture of a medicament for the improvement of cognitive dysfunction or learning and memory impairment. Furthermore, the present invention also relates to use of a 3-furan-2-cyano-2-acrylamide derivative shown as formula (I) or a pharmaceutically acceptable salt thereof in the manufacture of a medicament for the inhibition of EGFR or cytotoxicity of Aβ42. Furthermore, the present invention also relates to use of a 3-furan-2-cyano-2-acrylamide derivative shown as formula (I) or a pharmaceutically acceptable salt thereof in the manufacture of a medicament for the treatment or prophylaxis of vascular dementia or vascular cognitive disorders. Furthermore, the present invention also relates to use of a 3-furan-2-cyano-2-acrylamide derivative shown as formula (I) or a pharmaceutically acceptable salt thereof in the manufacture of a medicament for the treatment or prophylaxis of cholinergic neuron degenerative lesions.

Research and production of anti-senile dementia drugs has attracted great attention around the world, now a number of relevant biological activity screening and evaluation systems have been established, fruit fly is one of the most well-known biological models in the whole-animal models, with many advantages compared with other animal models, such as a very small individual occupying space, low feeding cost, easy cultivation, rapid propagation rate and strong fecundity (a high screening flux), small sample consumption (5-50 mg), short life period (about 50 days, a short activity test period), significant age-related neuronal degeneration, and is the ideal model forneuro degenerative diseases such as senile dementia research and drug screening.

As shown in activity-screening study of anti-senile dementia drugs using transgenic fruit fly as a model, the compound provided by the present invention could effectively improve the learning and memory ability of transgenic fruit flies with senile dementia, indicating that these compounds have significant therapeutic effect on neurodegenerative diseases such as senile dementia and could be used in the prophylaxis and treatment of neurodegenerative diseases including vascular dementia, vascular cognitive impairment, senile dementia, cholinergic neuron degenerative lesions, learning and memory impairment.

The present invention also relates to a pharmaceutical composition comprising a 3-furan-2-cyano-2-acrylamide derivative of formula (I) or a pharmaceutically acceptable salt thereof and one or more pharmaceutically acceptable additives.

The term "pharmaceutically acceptable salts" refers to modified derivatives obtained by parent compound thereof forming salts with acids or bases. Examples of pharmaceutically acceptable salts include, but are not limited to, inorganic or organic acid salts of basic residues (such as amines); alkali metal or organic salts of acidic residues (such as carboxylic acids); and the like. The pharmaceutically acceptable salts include the conventional non-toxic salts orquaternary ammonium salts formed by the parent compound, such as salts formed by non-toxic inorganic or organic acids. For example, the conventional non-toxic salts include salts obtained by inorganic acids such as hydrochloride, hydrobromide, sulfate, phosphate and nitrate and the like; and salts obtained by organic acids such as acetate, propionate, succinate, glycolate, stearate, lactate, malate, tartrate, citrate, ascorbate, pamoate, maleate, hydroxy maleate, phenyl maleate, glutamate, benzoate, salicylate, fumarate, toluenesulfonate, methanesulfonate, oxalate, and isethionate and the like.

If the compounds of the present invention are basic, the salts may be prepared by pharmaceutically acceptable nontoxic acids, including inorganic or organic acids. The acids include acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, nitric acid, pamoic acid, pantothenic acid, phosphoric acid, succinic acid, sulfuric acid, tartaric acid and p-toluenesulfonic acid and the like.

The pharmaceutical compositions of the present invention include any composition prepared by mixing the compounds of the present invention and pharmaceutically acceptable additives. "Pharmaceutically acceptable" means the carriers, diluents or excipients and other additives must be compatible with the other ingredients of the formulation and non-deleterious to the recipient thereof.

The compounds of this invention may be administered orally, parenterally (e.g., intramuscularly, intraperitoneally, intravenously, ICV, intracisternal injection or infusion, subcutaneous injection or implant), by inhalation spray, nasally, vaginally, rectally, sublingually or topically, and may be used singly or in combination with conventional non-toxic pharmaceutically acceptable carriers, adjuvants and excipients and other additives to form a unit formulation with a suitable dosage applicable to the various routes of administration.

The pharmaceutical compositions comprising the compounds of the present invention used for administration may be suitable unit dosage forms and prepared by any methods well known in the pharmaceutical art. All the methods include the step of mixing the active ingredients and one or more pharmaceutically acceptable additives. Typically, the pharmaceutical composition is prepared in the following manner: uniformly and closely mixing the active ingredient and a liquid additive or finely divided solid additive or both, and then shaping the product into the desired formulation. The pharmaceutical compositions comprise the active ingredients with a desired therapeutically effective amount for the disease process or condition.

The pharmaceutical compositions comprising the active ingredients may be prepared into suitable oral forms such as tablets, aqueous or oily suspensions, dispersible powders or granules, emulsions, hard or soft capsules, syrups and the like. Any method well known in the art of pharmaceutical formulations may be employed for the preparation of the compositions for oral administration, and the compositions may contain one or more additives selected from sweeteners, flavor enhancers, coloring agents and preservatives.

The tablets contain active ingredients and a nontoxic pharmaceutically acceptable additive suitable for the manufacture of tablets. The additives may be an inert diluent (e.g. calcium carbonate, sodium carbonate, lactose, calcium phosphate or sodium phosphate), granulating and disintegrating agent (e.g. corn starch or alginic acid), binding agent (e.g. starch, gelatin or acacia senegal) and lubricant (e.g. magnesium stearate, stearic acid or talc). The tablets may be uncoated or coated by known techniques to extend disintegration and absorption in the gastrointestinal tract, thus providing a long-lasting therapeutic effect. For example, tablets may use a time-delaying material (such as glyceryl monostearate or glyceryl distearate), and may be made into slow-release tablets by coating, and may be formulated into immediate release tablets.

Formulations for oral application may be hard gelatin capsules with active ingredient mixed with an inert solid diluent (e.g. calcium carbonate, calcium phosphate or kaolin), or soft capsules with active ingredient mixed with an aqueous or oily medium (e.g. peanut oil, liquid paraffin or olive oil).

Aqueous suspensions contain the active substances and a nontoxic pharmaceutically acceptable additive suitable for the manufacture of aqueous suspensions. The additives may be a suspending agent (e.g. sodium carboxymethylcellulose, methylcellulose, hydroxypropyl methylcellulose, sodium alginate, polyvinylpyrrolidone, acacia senegal), dispersing or wetting agent (e.g. lecithin, polyoxyethylene stearate, heptadecaethyleneoxycetanol, polyoxyethylene sorbitan monooleate). The aqueous suspensions may also contain one or more preservatives (e.g. ethyl p-hydroxybenzoate or n-propyl p-hydroxybenzoate), one or more coloring agents, one or more flavor enhancers, and one or more sweeteners (e.g. sucrose or saccharin).

Oily suspensions may be prepared by suspending the active ingredients in a vegetable oil (e.g. peanut oil, olive oil, sesame oil or coconut oil) or in a mineral oil (e.g. liquid paraffin). The oily suspensions may contain a thickening agent (e.g. beeswax, hard paraffin or cetyl alcohol). To the oily suspensions, sweeteners and flavor enhancers described above may be added, and an antioxidant (e.g. ascorbic acid) may be added.

The pharmaceutical compositions of the present invention may also be in the form of a water-in-oil emulsifier. The oily phase may be a vegetable oil (e.g. olive oil or peanut oil) or a mineral oil (e.g. liquid paraffin) or a mixture thereof. Suitable emulsifiers may be a natural gum (e.g. acacia senegal or gum tragacanth), natural phosphatide (e.g. soybean lecithin) and ester or partial ester derived from fatty acids and hexitol anhydrides (e.g. sorbitan monooleate) and condensation product formed by the said partial ester with ethylene oxide (e.g. polyoxyethylene sorbitan monooleate). The emulsifiers may also contain sweeteners or flavor enhancers.

Syrups may be prepared by employing sweeteners (e.g. glycerol, propylene glycol, sorbitol or sucrose). The syrups may contain wetting agents, preservatives and flavor enhancers and coloring agents.

The pharmaceutical compositions may be sterile injectable aqueous or oleaginous suspensions. The suspensions may be prepared by suitable dispersing or wetting agents and suspending agents described above according to the process known in the art.

The pharmaceutical compositions may also be in the form of suppositories for rectal administration. The suppositories may be prepared by mixing the drugs with a suitable non-irritating additive which is a solid at room temperature but a liquid at the rectal temperature. The additives may be cacao butter and polyethylene glycol.

For topical application, creams, ointments, gels, liquids, or suspensions and the like containing the compounds of the present invention may be used. Similarly, transdermal patches may also be used for topical administration.

The present invention also relates to a method for preparation of a 3-cyano-2-furan-2-acrylamide derivative of general formula (I) described above comprising:

(1) conducting an amidation reaction of cyanoacetic acid with a compound (2) $R_2NH_2$ under the presence of a condensing agent, to give a compound (3)

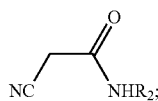

wherein, the organic solvent used is selected from the group consisting of toluene, xylene, chlorobenzene, acetonitrile, tetrahydrofuran, dioxane, dichloromethane, trichloromethane, carbon tetrachloride, diethyl ether, dipropyl ether, diisopropyl ether, methyl tert-butyl ether, hexane, cyclohexane, methylcyclohexane and n-heptane, and combinations thereof of any proportion;

the condensing agent is selected from the group consisting of 1-hydroxy-7-azabenzotriazole (HOAt), 1-hydroxybenzotrizole (HOBt), o-(7-azabenzotriazol-1-yl)-N,N,N',N'-tetramethyluronium hexafluorophosphate (HATU), 0-benzo-triazole-N,N,N',N'-tetramethyluroniumhexafluorophosphate (HBTU), bis(2-oxo-3-oxazolidiny)phosphonic chloride (BOP-Cl), 1H-benzotriazol-1-yloxytripyrrolidinophosphonium hexafluorophosphate (PyBOP), 1,3-dicyclohexylcarbodiimide (DCC),N,N'-carbonyldiimidazole (CDI), 1-(3-Dimethylaminopropyl)-3-ethylcarbodiimide (EDC), N,N'—N,N'-diisopropylcarbodiimide (DIC),4-dimethylaminopyridine (DMAP) and combinations thereof;

(2) conducting a condensation reaction of a compound (3)

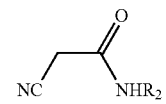

with a compound (4)

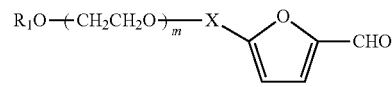

under the presence of a catalyst to prepare a compound of formula I;

wherein, the organic solvent used is selected from the group consisting of water, methanol, ethanol, n-propanol, isopropanol, n-butanol, isobutanol, dimethylformamide (DMF), dimethylacetamide, 1,3-dimethyl-2-imidazolidinone (DMI), dimethyl sulfoxide (DMSO), tetrahydrofuran, dioxane, acetonitrile, propionitrile, acetone, and combinations thereof of any proportion;

the catalyst is selected from the group consisting of potassium phosphate, sodium phosphate, potassium fluoride, sodium fluoride, zinc chloride, potassium chloride, sodium chloride, sodium bromide, potassium bromide, cadmium iodide, potassium iodide, sodium iodide, triethylbenzenemethanaminium chloride (TEBAC), cetyltrimethylammonium bromide (CTMAB), tetrabutylammonium iodide (TBAI), 1-methylpiperazine, potassium carbonate, sodium carbonate, cesium carbonate, calcium carbonate, dimethylamine, diethylamine, triethylamine, diisopropylethylamine, piperidine, pyridine, 1,8-diazabicyclo[5.4.0]undec-7-ene (DBU), 1,5-diazabicyclo [4.3.0] non-5-ene (DBN), tetrabutylammonium hydroxide and combinations thereof.

Another aspect of the invention is to provide an intermediate used for preparation of 3-furyl-2-cyano-2-acrylamide derivative shown as general formula (I) and pharmaceutical acceptable salt thereof, having a structure of formula (4):

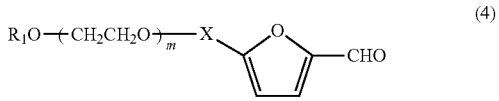

wherein $R_1$ is selected from the group consisting of H, $C_1$-$C_6$ alkyl, $C_2$-$C_6$ alkenyl, $C_2$-$C_6$ alkynyl and $C_3$-$C_6$ cycloalkyl; X is $(CH_2)_n$ or $(CH_2)_nY$, wherein n is an integer greater than or equal to zero; Y is NH, O or S; m is an integer greater than or equal to zero.

In an embodiment of the present invention, in the general formula (I) X is $(CH_2)_n$, where n is an integer greater than zero, preferably n is an integer of 1-10, more preferably n is an integer of 1-5, and more preferably n is 1, 2, 3, 4 or 5.

In an embodiment of the present invention, in the general formula (I) X is $(CH_2)_nY$, where n is an integer greater than or equal to zero, preferably n is an integer of 0-10, more preferably n is an integer of 0-5, and more preferably n is 0, 1, 2, 3, 4 or 5; Y is NH, O or S, preferably Y is NH.

In an embodiment of the present invention, in the general formula (I) X is $(CH_2)_nY$, wherein n is 0, 1, 2, Y is NH, preferably X is NH, $CH_2NH$.

In an embodiment of the present invention, in the general formula (I) m is an integer of 0-10, preferably m is an integer of 0-5, and more preferably m is 0, 1, 2, 3, 4 or 5.

In an embodiment of the present invention, in the general formula (I) $R_1$ is selected from H, $C_1$-$C_6$ alkyl, preferably H, $C_1$-$C_3$ alkyl, more preferably H, methyl, ethyl.

BRIEF DESCRIPTION OF THE DRAWINGS

FIG. 1 illustrates the comparison chart for the anti-senile dementia effect of 3-furan-2-cyano-2-acrylamide derivatives.

DETAILED DESCRIPTION OF THE INVENTION 1-bromo-2-(2-methoxyethoxy)ethane is purchased from Shenyang OllyChem Technology Co., Ltd., and other reagents are purchased from Sinopharm Chemical Reagent Co., Ltd. in Beijing.

Example 1: Preparation of 2-cyano-N-(4-fluorophenyl)-3-(5-hydroxymethyl-2-furyl)-2-acrylamide (JK-01A)

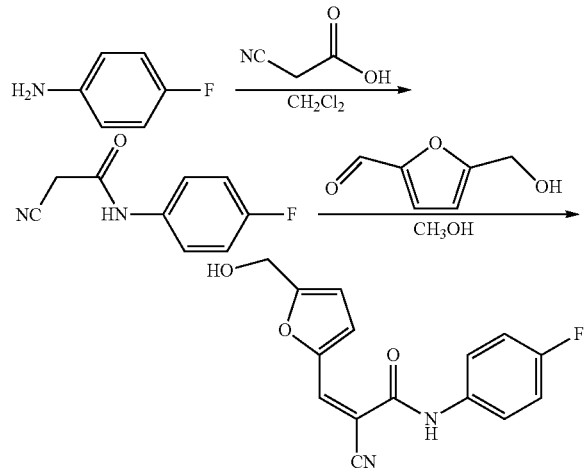

Step 1: Preparation of 2-cyano-N-(4-fluorophenyl) acetamide 4-fluoroaniline (11.1 g, 0.1 mol), 2-cyanoacetate acid (8.5 g, 0.1 mol), EDCI (19.2 g, 0.1 mol), HOBt (13.5 g, 0.1 mol) and $Et_3N$ (20.2 g, 0.2 mol) were dissolved in $CH_2Cl_2$ (200 mL), and stirred at room temperature overnight. Distilled water (100 mL) was added, the liquid layers obtained was separated, the aqueous layer was extracted with $CH_2Cl_2$ (50 mL×2), the mixed organic layer was successively washed with distilled water (50 mL×2) and saturated brine (50 mL×1), dried with $Na_2SO_4$, concentrated. The residue was separated by a silica gel column (PE/EA=3:1) to give 15.0 g of a white solid with a yield of 84.0%.

NMR Detection:
$^1$H NMR (400 MHz, DMSO-$d_6$): 3.89 (s, 2H), 7.18 (m, 2H), 7.56 (m, 2H), 10.39 (s, 1H).

Step 2: Preparation of 2-cyano-N-(4-fluorophenyl)-3-(5-hydroxymethyl-2-furyl)-2-acrylamide 2-cyano-N-(4-fluorophenyl) acetamide (2.0 g, 11.2 mmol), 5-(hydroxymethyl) furan-2-carbaldehyde (2.1 g, 16.8 mmol) and 1-methylpiperazine (1.1 g, 11.2 mmol) were dissolved in $CH_3OH$ (50 mL), and stirred at room temperature overnight. The solid was collected by filtration, washed with $CH_3OH$ (50 mL) to give 1.1 g of a yellow solid with a yield of 36.0%.

NMR Detection:
$^1$H NMR (400 MHz, DMSO-$d_6$): 4.54 (d, 2H), 5.56 (m, 1H), 6.68 (d, 1H), 7.20 (m, 2H), 7.41 (d, 1H), 7.68 (m, 2H), 8.07 (s, 1H), 10.26 (s, 1H).

Example 2: Preparation of 2-cyano-N-[2-(1H-indol-3-yl) ethyl]-3-(5-hydroxymethyl-2-furyl)-2-acrylamide (JK-03A)

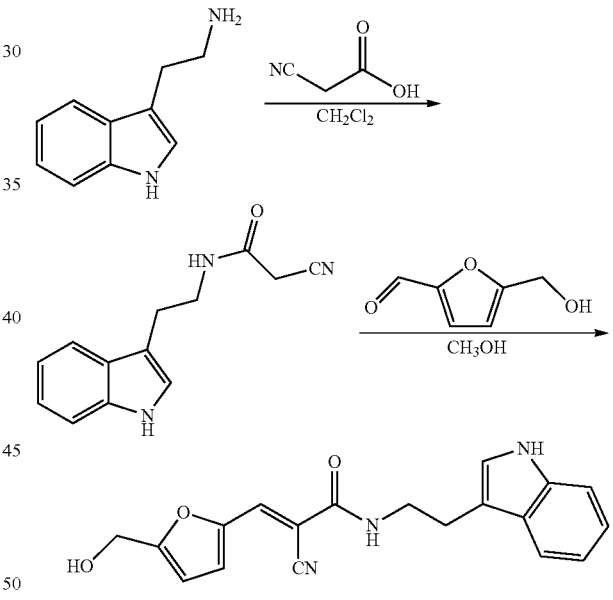

Step 1: Preparation of N-[2-(1H-indol-3-yl) ethyl]-2-cyano acetamide 2-(1H-indol-3-yl) ethylamine (16.0 g, 0.1 mol), 2-cyanoacetate acid (8.5 g, 0.1 mol), EDCI (19.2 g, 0.1 mol), HOBt (13.5 g, 0.1 mol) and $Et_3N$ (20.2 g, 0.2 mol) were dissolved in $CH_2Cl_2$ (200 mL), and stirred at room temperature overnight. Distilled water (100 mL) was added, the liquid layers obtained was separated, the aqueous layer was extracted with $CH_2Cl_2$ (80 mL×2), the mixed organic layer was successively washed with distilled water (80 mL×2) and saturated brine (80 mL×1), dried with $Na_2SO_4$, concentrated. The residue was separated by a silica gel column (PE/EA=1:1) to give 18.0 g of a white solid with a yield of 79.0%.

MS Detection:
MASS(ESI+) m/z=228 (M+H)+.

Step 2: Preparation of 2-cyano-N-[2-(1H-indol-3-yl) ethyl]-3-(5-hydroxymethyl-2-furyl)-2-acrylamide N-[2-(1H-indol-3-yl) ethyl]-2-cyanoacetamide (3.0 g, 13.2 mmol), 5-(hydroxymethyl) furan-2-carbaldehyde (1.1 g, 8.8 mmol) and 1-methylpiperazine (1.3 g, 13.2 mmol) were dissolved in CH$_3$OH (50 mL), and stirred at room temperature overnight. The solid was collected by filtration, washed with CH$_3$OH (50 mL) to give 1.7 g of a yellow solid with a yield of 58.0%.
NMR Detection:
$^1$H NMR (400 MHz, DMSO-d$_6$): 2.91 (m, 2H), 3.47 (m, 2H), 4.51 (d, 2H), 5.53 (m, 1H), 6.64 (d, 1H), 6.98 (m, 1H), 7.07 (m, 1H), 7.17 (d, 1H), 7.33 (m, 2H), 7.59 (m, 1H), 7.93 (s, 1H), 8.42 (s, 1H), 10.83 (s, 1H).

Example 3: Preparation of 2-cyano-N-[2-(1H-3-indolyl) ethyl]-3-{5-[2-(2-hydroxyethoxy) ethylamino]-2-furyl}-2-acrylamide (JK-05A)

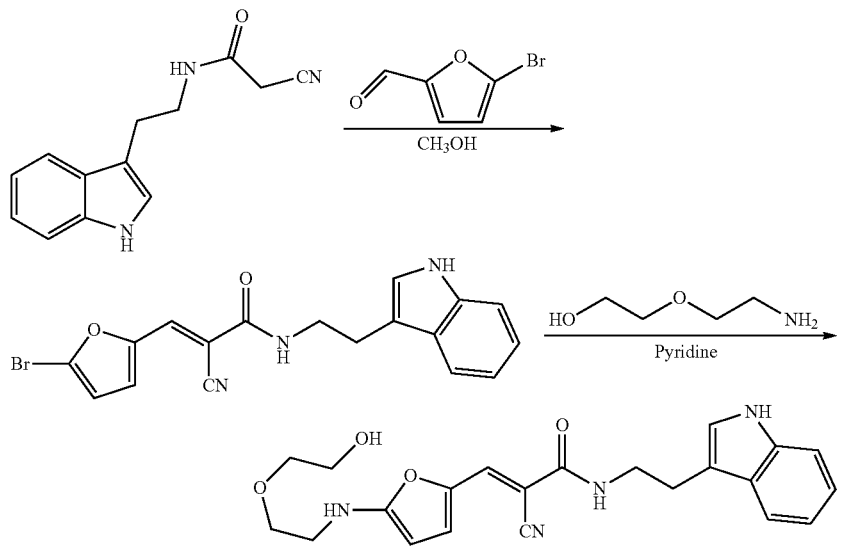

Step 1: Preparation of 2-cyano-N-[2-(1H-3-indolyl) ethyl]-3-(5-bromo-2-furyl)-2-acrylamide N-[2-(1H-indol-3-yl) ethyl]-2-cyanoacetamide (5.0 g, 22.0 mmol), 5-bromo-furan-2-carbaldehyde (2.5 g, 14.6 mmol) and 1-methylpiperazine (2.2 g, 22.0 mmol) were dissolved in CH$_3$OH (100 mL), and stirred at room temperature overnight. The solid was collected by filtration, washed with CH$_3$OH (50 mL) to give 4.5 g of a yellow solid with a yield of 81.0%.
MS Detection:
MASS(ESI$^+$) m/z=385 (M+H)$^+$.

Step 2: Preparation of 2-cyano-N-[2-(1H-3-indolyl) ethyl]-3-{5-[2-(2-hydroxyethoxy) ethylamino]-2-furyl}-2-acrylamide 2-cyano-N-[2-(1H-3-indolypethyl]-3-(5-bromo-2-furyl)-2-acrylamide (4.5 g, 11.7 mmol) and 2-(aminoethoxy) ethanol (2.54 g, 17.6 mmol) were dissolved in pyridine (30 mL), stirred at 40° C. overnight. The reaction mixture was concentrated under reduced pressure, and the residue was separated and purified by preparative liquid chromatography to give 1.2 g of a brown solid with a yield of 25.0%.
MS Detection:
MASS(ESI$^+$) m/z=409 (M+H)$^+$.

Example 4: Preparation of 2-cyano-N-(4-fluorophenyl)-3-[5-(2,5,8-trioxa-nonyl-1-yl)furan-2-yl]-2-acrylamide (JK-06A)

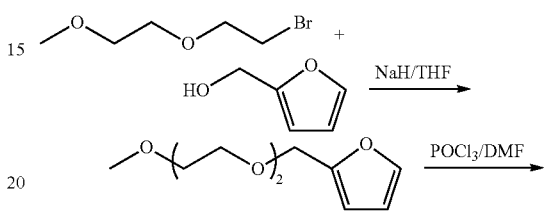

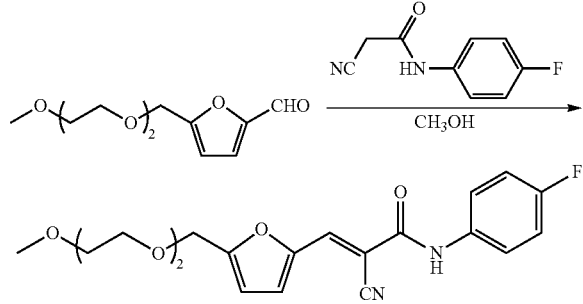

-continued

Step 1: Preparation of 2-(2,5,8-trioxa-nonyl-1-yl) furan

To a solution formed by furfuralcohol (2.0 g, 20.4 mmol) dissolved in tetrahydrofuran (100 mL) NaH (1.5 g, 61.3 mmol) was added, followed by the addition of 1-bromo-2-

(2-methoxyethoxy)ethane (7.5 g, 40.8 mmol), and the reaction liquid was stirred overnight. The reaction mixture was extracted with ethyl acetate, and the extract was washed with distilled water, dried with anhydrous sodium sulfate, concentrated to dryness under reduced pressure, the residue was purified by a silica gel column to give 3.5 g of a pale yellow oil with a yield of 85.7%.

MS Detection:
MASS(ESI⁺) m/z=223.1 (M+Na)⁺.

Step 2: Preparation of 5-(2,5,8-trioxa-nonyl-1-yl)furan-2-carbaldehyde

A mixed solution of DMF (1.7 g, 22.5 mmol) and 1,2-dichloroethane (45 mL) was stirred and cooled to 0° C., and POCl₃ (3.0 g, 20.1 mmol) was slowly added dropwise with a controlled dropping rate to make the temperature of the reaction solution lower than 25° C. To the reaction mixture, a solution formed by 2-(2,5,8-trioxa-nonyl-1-yl) furan (3.0 g, 15.0 mmol) dissolved in 1,2-dichloroethane (45 mL) was slowly added dropwise with a controlled dropping rate to make the temperature of the reaction solution lower than 25° C. The mixture obtained was stirred at room temperature overnight after completion of addition dropwise. To the reaction mixture, a saturated solution of sodium bicarbonate (200 mL) was slowly added dropwise, then extracted with diethyl ether (3×200 mL), the mixed extract was washed successively with distilled water and saturated sodium chloride solution, dried with anhydrous sodium sulfate, and concentrated to dryness under reduced pressure, the residue was purified by a silica gel column to give 3.1 g of a pale yellow oil with a yield of 91.3%.

MS Detection:
MASS(ESI⁺) m/z=251.2 (M+Na)⁺.

Step 3: Preparation of 2-cyano-N-(4-fluorophenyl)-3-[5-(2,5,8-trioxa-nonyl-1-yl)furan-2-yl]-2-acrylamide (JK-06A)

2-cyano-N-(4-fluorophenyl)acetamide (4.0 g, 22.4 mmol), 5-(2,5,8-trioxa-nonyl-1-yl)furan-2-carbaldehyde (3.4 g, 14.9 mmol) and 1-methylpiperazine (2.2 g, 22.4 mmol) were dissolved in CH₃OH (50 mL), stirred at room temperature overnight. The solid was collected by filtration, washed with CH₃OH (50 mL) to give 1.6 g of a yellow solid with a yield of 27.6%.

MS Detection:
MASS(ESI⁺) m/z=411.3 (M+Na)⁺.

Example 5: Preparation of 2-cyano-N-[2-(1H-3-indolyl) ethyl]-3-[5-(1, 4,7,10-tetraoxa-undecane-11-yl)furan-2-yl]-2-acrylamide (JK-07A)

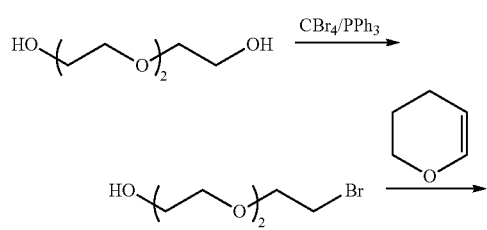

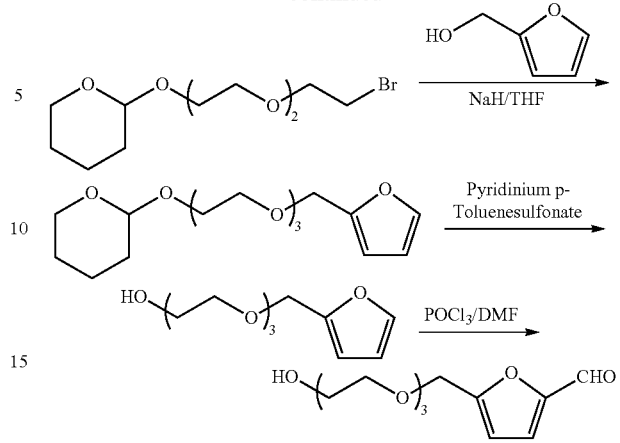

Step 1: Preparation of 2-[2-(2-bromoethoxy)ethoxy] ethanol

Triglycol (12.2 g, 81.3 mmol) was dissolved in dichloromethane (150 mL), stirred and cooled to 0° C., and then carbon tetrabromide (12.0 g, 27.1 mmol) and triphenylphosphine (7.8 g, 29.8 mmol) were added. The reaction mixture was stirred at room temperature for 2 h, the solvent was distilled off under reduced pressure, the residue was purified by a silica gel column to give 4.8 g of a pale yellow oil with a yield of 27.7%.

NMR Detection:
¹H NMR (400 MHz, CDCl₃): 3.35 (t, 2H), 3.44 (t, 2H), 3.53 (m, 4H), 3.58 (t, 2H), 3.68 (t, 2H).

Step 2: Preparation of 2-(8-bromo-3,6-dioxa-octane-1-yl)tetrahydropyran

2-[2-(2-bromoethoxy) ethoxy]ethanol (4.2 g, 19.8 mmol) was dissolved in diethyl ether (150 mL), slowly added dropwise by 3,4-dihydro-2H-pyran (2.5 g, 29.7 mmol) under stirring, the reaction mixture was stirred at room temperature for 1 h. To the reaction liquid, NaHCO₃ was added for neutralization, then the reaction mixture was filtered, evaporated under reduced pressure to remove the solvent and excess 3,4-dihydro-2H-pyran, the residue was purified by a silica gel column to give 4.1 g of a pale yellow oil with a yield of 69.7%. NMR detection:
¹H NMR (400 MHz, CDCl₃): 1.40-1.85 (m, 6H), 3.35-3.85 (m, 14H), 4.55-4.62 (m, 1H).

Step 3: Preparation of 2-[10-(furan-2-yl)-3,6,9-trioxa-decane-1-yl]tetrahydropyran To a solution formed by furfuralcohol (2.0 g, 20.4 mmol) dissolved in tetrahydrofuran (100 mL) NaH (1.5 g, 61.3 mmol) was added, followed by addition of 2-(8-bromo-3,6-dioxa-octane-1-yl)tetrahydropyran (12.1 g, 40.8 mmol), and the reaction liquid was stirred overnight. The reaction mixture was extracted with ethyl acetate, and the extract was washed with distilled water, dried with anhydrous sodium sulfate, concentrated to dryness under reduced pressure, the residue was purified by a silica gel column to give 5.1 g of a pale yellow oil with a yield of 79.5%.

MS Detection:
MASS(ESI⁺) m/z=337 (M+Na)⁺.

Step 4: Preparation of 2-(10-hydroxy-2,5,8-trioxa-decane-1-yl)furan

Pyridine p-toluenesulfonate (3.1 g, 14.0 mmol) was dissolved in absolute ethanol (150 mL), 2-[10-(furan-2-yl)-3,6,9-trioxa-decane-1-yl]tetrahydropyran (4.0 g, 12.7 mmol) was then added. The reaction mixture was warmed to 55° C., stirred for 12 h with heat preservation, concentrated to dryness under reduced pressure, the residue was purified by a silica gel column to give 2.4 g of a pale yellow oil with a yield of 82.1%.

MS Detection:
MASS(ESI$^+$) m/z=253 (M+Na)$^+$.

Step 5: Preparation of 5-(10-hydroxy-2,5,8-trioxa-decane-1-yl)furan-2-carbaldehyde A mixed solution of DMF (1.7 g, 22.5 mmol) and 1,2-dichloroethane (45 mL) was stirred and cooled to 0° C., then POCl$_3$ (3.0 g, 20.1 mmol) was slowly added dropwise with a controlled dropping rate to make the temperature of the reaction solution lower than 25° C. To the reaction mixture, a solution formed by 2-(10-hydroxy-2,5,8-trioxa-decane-1-yl)furan (3.5 g, 15.0 mmol) dissolved in 1,2-dichloroethane (45 mL) was slowly added dropwise with a controlled dropping rate to make the temperature of the reaction solution lower than 25° C. The mixture obtained was stirred at room temperature overnight after completion of addition dropwise. To the reaction mixture, a saturated solution of sodium bicarbonate (200 mL) was slowly added dropwise, then extracted with diethyl ether (3×200 mL), the mixed extract was washed successively with distilled water and saturated sodium chloride solution, dried with anhydrous sodium sulfate, and concentrated to dryness under reduced pressure, the residue was purified by a silica gel column to give 3.4 g of a pale yellow oil with a yield of 87.8%.

MS Detection:
MASS(ESI$^+$) m/z=281 (M+Na)$^+$.

Step 6: Preparation of 2-cyano-N-[2-(1H-3-indolyl)ethyl]-3-[5-(10-hydroxy-2,5,8-trioxa-decane-1-yl)-2-furanyl]-2-acrylamide N-[2-(1H-indol-3-yl) ethyl]-2-cyanoacetamide (5.0 g, 22.0 mmol), 5-(10-hydroxy-2,5,8-trioxa decane-1-yl)furan-2-carbaldehyde (3.8 g, 14.6 mmol) and 1-methylpiperazine (2.2 g, 22.0 mmol) were dissolved in CH$_3$OH (100 mL), stirred at room temperature overnight. The solid was collected by filtration, washed with CH$_3$OH (50 mL) to give 5.3 g of a yellow solid with a yield of 77.6%.

MS Detection:
MASS(ESI$^+$) m/z=490 (M+Na)$^+$.

Example 6: Test for Anti-Senile Dementia Effect of Compounds JK-01A, JK-03A, JK-05A, JK-06A and JK-07A Feeding of Fruit Flies with Senile Dementia:

In all tests, w$^{1118}$ (isoCJ1) was used as a control gene system, referred to as the "2U". Progeny fruit flies with disease carrying P35 and H29.3 were obtained by integration of fruit flies carrying elav-GAL4$^{c155}$ (referred to as P35) and fruit flies carrying Aβ42 (UAS-Aβ42; referred to as H29.3). The first generation of fruit flies obtained by hybridization was used for behavioral testing. Details as follows:

Control Fruit Flies:

| F0 | 2U ♀<br>(w/w; +/+) | × | H29.3 ♂<br>(w/Y; UAS-Aβ42/cyo) or<br>(+/Y; UAS-Aβ42/cyo) |
|---|---|---|---|
| F1 | | 2U*H29.3 ♂<br>(+/Y; UAS-Aβ42/+) | |

AD Fruit Flies:

| F0 | P35 ♀<br>(elav/elav;<br>+/+) | × | H29.3 ♂<br>(w/Y; UAS-Aβ42/cyo) |
|---|---|---|---|
| F1 | | AD ♂<br>(elav/Y; UAS-Aβ42/+; +/+) | |

Feeding of AD Fruit Flies:

All the fruit flies were reared in an environment with a temperature of 24° C., relative humidity of 40% RH. On the first day, newborn male 2U*H29.3 fruit flies and male AD fruit flies were picked out and put into glass bottles (there were about 120 fruit flies in each bottle). During administration period, these fruit flies were placed in an environment with a temperature of 28° C., relative humidity of 42% RH. From the second day to the eighth day, the fruit flies were transferred into new glass bottles 4 hours later after administration. All the fruit flies were placed in an environment with a temperature of 28° C., relative humidity of 42% RH until 1 hour before Pavlovian olfactory learning test.

Administration for AD Fruit Flies

On the first day of eclosion dispensation of drugs was conducted, the second day administration was carried out. The respective initial amount of compounds JK-01A, JK-03A, JK-05A, JK-06A and JK-07A was 10 mg, and the final concentration was 100 μM. Each group had two glass bottles of flies which were administered 50 μl within seven days (from the second day to the eighth day). During administration period, since some fruit flies died naturally or for other causes, about 100 flies were remained in each bottle when Pavlovian olfactory test was conducted on the ninth day.

Pavlovian Olfactory Learning Test:

The fruit flies were placed on the automatic training device for training. In training, a group of about 100 flies first contacted with one kind of odor (octanol or methyl cyclohexanol) accompanied by electric shocks (an electric shock of 60 V for 3.5 s at 1.5-s intervals) for 60 s, rested at 45-s intervals, and then contacted with another kind of odor (methyl cyclohexanol or octanol) without electric shocks for 60 s. To test the "immediate memory" (also called "learning"), flies after the training were immediately sent to the T-maze choice point, and allowed to choose between two kinds of odor, the learning and memory index PI (Performance index) in every test was calculated according to the number of flies choosing each kind of odor. PI=0 represented 50:50, meaning that fruit flies could not remember the odor accompanied by electric shocks, PI=100 represented that 100% of the flies remembered the odor accompanied by electric shocks. Learning test was carried out in a darkroom with a temperature of 25° C., relative humidity of 70% RH. The fruit flies entered the darkroom to be familiar with the environment 1 hour before test.

Statistical Analysis:

The test data was analyzed and plotted by employing GraphPad Prism.

Test Results:

In the activity test, the olfactory short-term memory impairment tests of healthy flies with the same genetic background and without administration, AD flies without administration, AD flies administrated positive or negative control drugs and AD flies administrated test drugs were carried out at the same time, their learning and memory indexes were calculated, and the learning and memory index of AD flies administrated test drugs was compared with those of healthy flies with the same genetic background, AD flies, AD flies administrated positive or negative control drugs to evaluate the anti-senile dementia effect of test compounds. A relatively higher learning and memory index of AD flies administrated test drugs represented a stronger anti-senile dementia effect of test compounds.

Comparison between learning and memory indexes of AD flies administrated test drugs and AD flies without administration (only administrated drug sample-free solvent) was conducted by employing T test, a P value less than 0.05 represented a difference, a P value less than 0.01 represented a significant difference, a P value less than 0.001 represented a very significant difference.

The test results are shown in Table 1, the data in Table 1 is plotted as shown in FIG. 1:

TABLE 1

Comparison of anti-senile dementia effect of drugs

| Genotype/drug | PI (mean value) | S.E.M | T test |
|---|---|---|---|
| 2U | 90 | 1.22 | |
| 2U*H29.3 | 61 | 4.15 | |
| P35*H29.3 | 26 | 3.82 | |
| PC | 62 | 1.65 | 0.0001 |
| JK-01A | 65 | 0.28 | 0.0025 |
| JKF-006 | 37 | 2.68 | 0.1531 |
| JK-03A | 56 | 3.02 | 0.0077 |
| JKF-027 | 54 | 6.08 | 0.0144 |
| JK-05A | 40 | 0.85 | 0.0794 |
| JKF-011 | 50 | 1.11 | 0.0139 |
| JK-06A | 67 | 0.34 | 0.0024 |
| JK-07A | 58 | 2.98 | 0.0082 |
| Crocetin | 40 | 4.81 | 0.0935 |
| Dasatinib | 56 | 4.62 | 0.0095 |
| Erlotinib | 48 | 1.37 | 0.0192 |

The test data in Table 1 showed that, compared with drugs crocetin, erlotinib, dasatinib, JKF-006, JKF-027 and JKF-011 (disclosed in WO2012/103282A2) reported to had an anti-senile dementia effect, compounds JKF-006, JK-05A and crocetin (P>0.05) had equivalent anti-senile dementia effects, compounds JKF-027, JKF-011 and erlotinib (P<0.05) had anti-senile dementia effects, compounds JK-01A, JK-03A, JK-06A, JK-07A and dasatinib (P<0.01) had significant anti-senile dementia effects.

Test data also showed that the compounds of the present invention JK-01A, JK-03A, JK-06A and JK-07A had more significant anti-senile dementia effects compared with compound JKF-006, JKF-027 and JKF-011.

Thus, the compounds of the present invention JK-01A, JK-03A, JK-05A, JK-06A and JK-07A may be used for treatment or prophylaxis of Alzheimer's disease, senile dementia, neurodegenerative disease, vascular dementia, vascular cognitive impairment, cholinergic neuron degenerative lesions, and helpful for the improvement of cognitive dysfunction or learning and memory impairment.

Example 7: Preliminary Acute Toxicity Test for Compounds JK-01A, JK-03A, JK-05A, JK-06A and JK-07A Method: in the acute toxicity test, ICR mice were used and divided into six groups for administration, with 10 mice in each group and half male and half female. Due to limitations of administration concentration and dosing volume, each test drug had the maximum dosage of 6 g/kg/day, and administered orally twice with an interval of 3 hours. The control group was administrated the same volume of vehicle. Observation was conducted for 14 consecutive days after administration.

Results: during the observation period, in test drug groups, no animal died; no significant difference between indexes such as action, mental state, haircolor and the like of animals in each test drug group and vehicle group was obtained by clinical observation. Additionally, the gross anatomy results showed no visible lesions in organs of animals in each test drug group. Therefore, these compounds were considered to be with a very low toxicity, and did not cause any death of the animal with a dosage of 4-6 g/kg/day, while no abnormal clinical manifestations were observed, the acute toxicity test results for each compound are shown in Table 2.

TABLE 2

Acute toxicity results of compounds

| No. | Test drug | Number of animals | Dosage (mg/kg/d) | Route of administration | Test result |
|---|---|---|---|---|---|
| 1 | Vehicle | 10 | 6000 | p.o. | No death, no abnormal reaction |
| 2 | Jk-01A | 10 | 4000 | p.o. | No death, no abnormal reaction |
| 3 | JK-03A | 10 | 6000 | p.o. | No death, no abnormal reaction |
| 4 | JK-05A | 10 | 5000 | p.o. | No death, no abnormal reaction |
| 5 | JK-06A | 10 | 6000 | p.o. | No death, no abnormal reaction |
| 6 | JK-07A | 10 | 4000 | p.o. | No death, no abnormal reaction |

The invention claimed is:

1. A compound of formula I, or a pharmaceutical acceptable salt thereof:

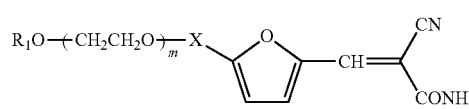

wherein $R_1$ is H; $R_2$ is aryl substituted by halogen; X is $(CH_2)_n$ or $(CH_2)_nY$, wherein n is an integer greater than or equal to zero; Y is NH, O or S; and m is an integer greater than or equal to zero.

2. The compound or pharmaceutical acceptable salt thereof according to claim 1, wherein n is 0, 1, 2, 3, 4 or 5.

3. The compound or pharmaceutical acceptable salt thereof according to claim 1, wherein m is 0, 1, 2, 3, 4 or 5.

4. The compound or pharmaceutical acceptable salt thereof according to claim 1, wherein $R_2$ is halophenyl.

5. The compound or pharmaceutical acceptable salt thereof according to claim 4, wherein $R_2$ is selected from the group consisting of p-fluorophenyl, p-chlorophenyl, and p-bromophenyl.

6. The compound or pharmaceutical acceptable salt thereof according to claim 1, wherein the compound is selected from the group consisting of:

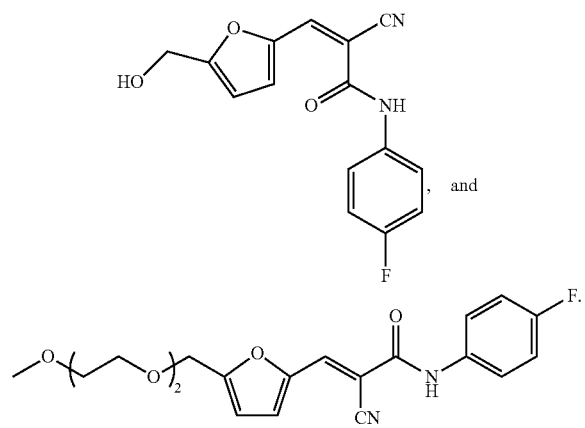

7. A compound of formula I, or a pharmaceutical acceptable salt thereof:

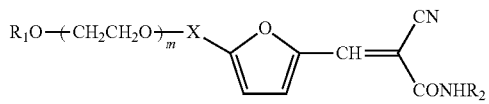

wherein $R_1$ is selected from the group consisting of H, $C_1$-$C_6$ alkyl, $C_2$-$C_6$ alkenyl, $C_2$-$C_6$ alkynyl and $C_3$-$C_6$ cycloalkyl; $R_2$ is selected from the group consisting of alkyl, cycloalkyl, alkenyl, alkynyl, heteroaryl, and heteroaralkyl; X is $(CH_2)_n$ or $(CH_2)_nY$, wherein n is an integer greater than or equal to zero; Y is NH, O or S; and m is an integer greater than or equal to zero.

8. The compound or pharmaceutical acceptable salt thereof according to claim 7, wherein n is 0, 1, 2, 3, 4 or 5.

9. The compound or pharmaceutical acceptable salt thereof according to claim 7, wherein m is 0, 1, 2, 3, 4 or 5.

10. The compound or pharmaceutical acceptable salt thereof according to claim 7, wherein $R_1$ is selected from the group consisting of methyl and ethyl.

11. The compound or pharmaceutical acceptable salt thereof according to claim 7, wherein $R_2$ is selected from the group consisting of $C_6$-$C_{15}$ heteroaryl, and $C_6$-$C_{15}$ heteroaralkyl.

12. The compound or pharmaceutical acceptable salt thereof according to claim 11, wherein $R_2$ is

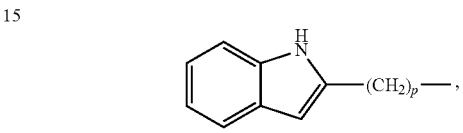

wherein p is an integer of 0-5.

13. The compound or pharmaceutical acceptable salt thereof according to claim 12, wherein p is 0, 1, 2, 3.

14. The compound or pharmaceutical acceptable salt thereof according to claim 7, wherein the compound is selected from the group consisting of:

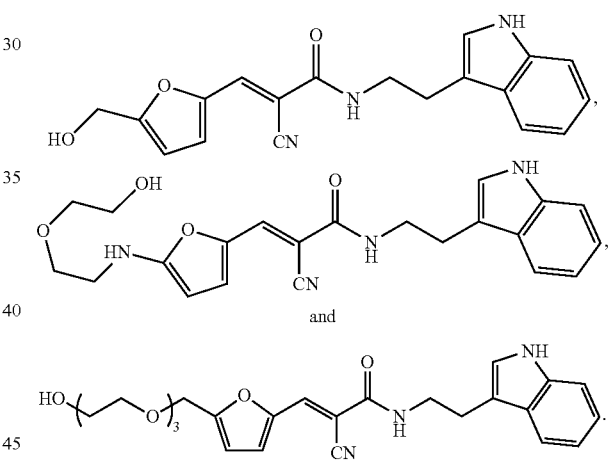

* * * * *